US012478747B2

(12) United States Patent
Knoch

(10) Patent No.: US 12,478,747 B2
(45) **Date of Patent: *Nov. 25, 2025**

(54) AEROSOL DELIVERY DEVICE AND OPERATING METHOD FOR THE AEROSOL DELIVERY DEVICE

(71) Applicant: PARI Pharma GmbH, Starnberg (DE)

(72) Inventor: Martin Knoch, Garmisch-Partenkirchen (DE)

(73) Assignee: PARI Pharma GmbH, Starnberg (DE)

( * ) Notice: Subject to any disclaimer, the term of this patent is extended or adjusted under 35 U.S.C. 154(b) by 109 days.

This patent is subject to a terminal disclaimer.

(21) Appl. No.: 18/081,774

(22) Filed: Dec. 15, 2022

(65) Prior Publication Data

US 2023/0119086 A1 Apr. 20, 2023

Related U.S. Application Data

(63) Continuation of application No. 15/535,889, filed as application No. PCT/EP2015/080262 on Dec. 17, 2015, now Pat. No. 11,547,822.

(30) Foreign Application Priority Data

Dec. 23, 2014 (EP) .................................... 14200105

(51) Int. Cl.
*A61M 15/00* (2006.01)
*A61M 16/00* (2006.01)
*A61M 16/06* (2006.01)

(52) U.S. Cl.
CPC ........ *A61M 15/00* (2013.01); *A61M 15/0085* (2013.01); *A61M 2016/0024* (2013.01);
(Continued)

(58) Field of Classification Search
CPC .............. A61M 15/00; A61M 15/0085; A61M 15/0086; A61M 15/0091; A61M 11/00;
(Continued)

(56) References Cited

U.S. PATENT DOCUMENTS

| | | | |
|---|---|---|---|
| 5,363,842 | A | 11/1994 | Mishelevich |
| 5,415,161 | A | 5/1995 | Ryder |

(Continued)

FOREIGN PATENT DOCUMENTS

| | | | |
|---|---|---|---|
| DE | 100 22 795 | A1 | 11/2001 |
| DE | 102 26 334 | A1 | 1/2004 |

(Continued)

OTHER PUBLICATIONS

International Search Report and Written Opinion dated Feb. 16, 2016, in connection with International Application No. PCT/EP2015/080262.

(Continued)

*Primary Examiner* — Joseph D. Boecker
(74) *Attorney, Agent, or Firm* — Wolf, Greenfield & Sacks, P.C.

(57) ABSTRACT

The invention relates to an aerosol delivery device comprising an aerosol generator for generating an aerosol in the aerosol delivery device, a sensor configured to detect a use of the aerosol delivery device for aerosol treatment, and a controller configured to deactivate the aerosol generator if no use of the aerosol delivery device for aerosol treatment is detected by the sensor. Further, the invention relates to a method for operating an aerosol delivery device, comprising the steps of operating an aerosol generator for generating an aerosol in the aerosol delivery device, detecting a use of the aerosol delivery device for aerosol treatment by means of a sensor, and deactivating the aerosol generator by means of
(Continued)

a controller if no use of the aerosol delivery device for aerosol treatment is detected by the sensor.

26 Claims, 2 Drawing Sheets

(52) U.S. Cl.
CPC ..... *A61M 2016/0027* (2013.01); *A61M 16/06* (2013.01); *A61M 2205/13* (2013.01); *A61M 2205/18* (2013.01); *A61M 2205/3334* (2013.01); *A61M 2205/3368* (2013.01); *A61M 2205/3375* (2013.01); *A61M 2205/44* (2013.01); *A61M 2205/502* (2013.01)

(58) Field of Classification Search
CPC .............. A61M 11/005; A61M 16/024; A61M 16/0816; A61M 16/14; A61M 16/147; A61M 2016/0018; A61M 2016/0021; A61M 2016/0024; A61M 2016/0033; A61M 2016/0039; A61M 2205/13
See application file for complete search history.

(56) References Cited

U.S. PATENT DOCUMENTS

| | | | | |
|---|---|---|---|---|
| 5,518,179 | A | 5/1996 | Humberstone et al. | |
| 5,957,389 | A | 9/1999 | Wunderlich et al. | |
| 6,269,810 | B1 * | 8/2001 | Brooker | A61M 15/0065 128/203.29 |
| 6,845,770 | B2 | 1/2005 | Klimowicz et al. | |
| 6,962,151 | B1 | 11/2005 | Knoch | |
| 7,331,339 | B2 | 2/2008 | Smith et al. | |
| 7,748,377 | B2 | 7/2010 | Smith | |
| 7,971,588 | B2 | 7/2011 | Fink et al. | |
| 7,980,247 | B2 | 7/2011 | Boehm et al. | |
| 8,196,573 | B2 | 6/2012 | Fink et al. | |
| 8,807,131 | B1 | 8/2014 | Tunnell | |
| 11,547,822 | B2 * | 1/2023 | Knoch | A61M 15/00 |
| 2003/0140921 | A1 | 7/2003 | Smith | |
| 2004/0016433 | A1 | 1/2004 | Estes | |
| 2006/0054166 | A1 | 3/2006 | Knoch | |
| 2007/0068513 | A1 | 3/2007 | Kreutzmann et al. | |
| 2007/0209659 | A1 | 9/2007 | Ivri et al. | |
| 2008/0142002 | A1 | 6/2008 | Fink et al. | |
| 2008/0251068 | A1 | 10/2008 | Schuschnig et al. | |
| 2009/0038610 | A1 | 2/2009 | Bogh | |
| 2009/0114737 | A1 | 5/2009 | Yu et al. | |
| 2010/0282247 | A1 * | 11/2010 | Kadrichu | A61M 15/0086 128/200.14 |
| 2011/0247620 | A1 | 10/2011 | Armstrong | |
| 2012/0037154 | A1 | 2/2012 | Gallem et al. | |
| 2012/0085344 | A1 | 4/2012 | Luber et al. | |
| 2013/0112197 | A1 | 5/2013 | Krüner et al. | |
| 2013/0269685 | A1 | 10/2013 | Wachtel | |
| 2015/0099994 | A1 * | 4/2015 | Spencer | A61M 15/0085 600/533 |
| 2015/0174349 | A1 * | 6/2015 | Tunnell | A61M 15/009 128/200.14 |
| 2015/0335074 | A1 | 11/2015 | Leung | |
| 2017/0368282 | A1 | 12/2017 | Knoch | |

FOREIGN PATENT DOCUMENTS

| | | | |
|---|---|---|---|
| EP | 1 927 373 | A1 | 6/2008 |
| EP | 2 030 644 | A1 | 3/2009 |
| JP | 2013/099544 | A | 5/2013 |
| WO | WO 02/36181 | A2 | 5/2002 |
| WO | WO 2010/066714 | A1 | 6/2010 |

OTHER PUBLICATIONS

International Preliminary Report on Patentability dated Jul. 6, 2017, in connection with International Application No. PCT/EP2015/080262.

European Search Report dated Jun. 2, 2015, in connection with European Application No. EP 14200105.

* cited by examiner

AEROSOL DELIVERY DEVICE AND OPERATING METHOD FOR THE AEROSOL DELIVERY DEVICE

CROSS REFERENCE TO RELATED APPLICATIONS

This application is a continuation of U.S. application Ser. No. 15/535,889, filed Jun. 14, 2017, now U.S. Pat. No. 11,547,822, which is a national stage of PCT/EP2015/080262, filed Dec. 17, 2015, which claims priority to EP 14200105.6, filed Dec. 23, 2014, which are hereby incorporated by reference in their entirety.

FIELD OF THE INVENTION

The invention relates to an aerosol delivery device comprising an aerosol generator for generating an aerosol in the device and a method for operating this aerosol delivery device.

BACKGROUND ART

Aerosols for therapeutic purposes are generated and delivered to a desired location within a user's or patient's body with aerosol delivery devices. A fluid (i.e., medicament) to be aerosolised or nebulised is supplied to an aerosol generator of the aerosol delivery device, the fluid is aerosolised or nebulised by the aerosol generator and the resultant aerosol is supplied to a user or patient. The fluid to be aerosolised or nebulised may be, for example, stored in a fluid reservoir of the aerosol delivery device or in an ampoule that can be inserted in the device.

The requirements placed on the aerosol delivery device arise from the treatment to be performed with the aerosols. One of these requirements concerns dosage accuracy and consistency, i.e., the accuracy and consistency of the administered quantity of the medicament provided as an aerosol. Only if the dosage of a medicament administered to a user or patient is accurately and consistently established, a precise and effective treatment with highly effective medicaments can be carried out.

In order to provide a high dosage accuracy and consistency, it has to be ensured that the aerosol generated by the aerosol generator is efficiently supplied to the user or patient without the occurrence of substantial aerosol losses inside or outside the aerosol delivery device.

Two different modes of aerosol administration are commonly used in aerosol treatment or therapy, namely continuous nebulisation and breath-triggered nebulisation.

Continuous nebulisers continuously generate aerosol during the aerosol treatment or therapy. These nebulisers offer the advantage of a simple structure and the quick administration of a desired aerosol dosage. However, substantial aerosol losses occur during exhalation of the user or patient and during intentional or unintentional interruptions of the treatment or therapy.

US-A-2006/0054166 discloses an inhalation nebuliser which allows for aerosol losses occurring during exhalation of a regularly breathing user or patient to be minimised. This inhalation nebuliser comprises an aerosol generator and a mixing chamber, wherein the aerosol generator continuously produces an aerosol.

The mixing chamber has an inhalation valve that allows ambient air to flow into the mixing chamber during an inhalation phase, while preventing aerosol from escaping during an exhalation phase. Further, the mixing chamber has an exhalation valve that allows discharge of the patient's respiratory air during the exhalation phase, while preventing an inflow of ambient air during the inhalation phase.

The exhalation valve ensures that the patient's exhaled air is vented to the surroundings without significantly reaching the mixing chamber. During the exhalation phase, the continuously operating aerosol generator accumulates or concentrates the aerosol in the mixing chamber, so that during an inhalation phase not only the amount of aerosol generated due to the continuous production is available for the inhalation, but at the beginning of the inhalation phase an aerosol bolus can be inhaled, which is available because of aerosol accumulation during the exhalation phase.

Nebulisers adopting such an approach are also disclosed in EP-A-1 927 373 and US-A-2012/0037154.

The aerosol losses increase considerably and become indeterminable if a user's or patient's regular respiration through the aerosol delivery device is interrupted. Hence, in the case of such an interruption, it is impossible to accurately determine the amount of aerosol delivered to the desired location within the user's or patient's body. Therefore, such interruptions significantly affect the accuracy and consistency of the administered aerosol dosage, thus lowering the efficiency of the aerosol treatment or therapy.

In order to minimise the aerosol losses occurring during such interruptions, some aerosol delivery devices with continuous nebulisers have been provided with a manual pause function, allowing for the nebuliser to be manually paused in the case of an interruption. However, such a manual pausing of the nebuliser is not sufficiently quick and reliable for ensuring an accurate and consistent administration of the generated aerosol.

In breath-triggered nebulisers, the aerosol generation is periodically switched on and off at the beginning and end of the inhalation phase, respectively, in order to minimise aerosol losses during exhalation periods of a user or patient. Aerosol generators of this type are disclosed, for example, in U.S. Pat. No. 7,748,377 and US-A-2008/0142002.

The aerosol generating system disclosed in U.S. Pat. No. 7,748,377 includes an aerosol generator, a controller and a breathing sensor. The controller is in communication with the aerosol generator to control the sequence of aerosolisation of a liquid for delivery to a patient. The breathing sensor is used to measure a breathing pattern of the patient, a peak flow, a breathing rate, exhalation parameters or a regularity of breathing. The measured breathing characteristics are routed to the controller and processed via a software algorithm to determine an appropriate sequence of delivery relative to the measured breathing cycle of the patient.

US-A-2008/0142002 discloses a method and a system for nebulising a liquid. The method comprises taking one or more breaths and measuring characteristics of the breath. An aerosol generator is operated based on the measured characteristics of the one or more measured breaths.

With such breath-triggered nebulisers, the aerosol losses occurring during exhalation periods of a user or patient can be considerably reduced. However, the administration of a desired aerosol dosage requires significantly more time than for the case of continuous nebulisers, thus potentially affecting patient adherence and the effectiveness of the aerosol treatment or therapy.

Hence, there remains a need for a simple aerosol delivery device and a simple aerosol delivery method, enabling the supply of an aerosol to a user or patient in a quick and efficient manner.

SUMMARY OF THE INVENTION

One object of the invention is to provide a simple aerosol delivery device which allows for an aerosol treatment to be carried out in a quick and efficient manner. Further, the invention aims to provide a method for operating this aerosol delivery device. These goals are achieved by a device with the technical features of claim 1 and a method with the technical features of claim 10. Preferred embodiments of the invention follow from the dependent claims.

The invention provides an aerosol delivery device comprising an aerosol generator for generating an aerosol in the aerosol delivery device, a sensor configured to detect a use of the aerosol delivery device for aerosol treatment, and a controller, e.g., a control unit, configured to deactivate or switch off the aerosol generator if no use of the aerosol delivery device for aerosol treatment or therapy is detected by the sensor.

The sensor is configured to detect whether the aerosol delivery device is being used for an aerosol treatment or aerosol therapy, such as an aerosol inhalation treatment or therapy, e.g., by a user or patient. Hence, the sensor is arranged to detect whether or not the aerosol delivery device is in use by a user or patient.

Herein, the expression "use of the aerosol delivery device for aerosol treatment" refers to a use of the device by a user or patient in which the user or patient respires, e.g., regularly respires, at least partly through the device. In this way, a desired dosage of the aerosol generated by the aerosol generator is supplied to a desired location within the user's or patient's body. The sensor may detect the use of the aerosol delivery device for aerosol treatment by detecting whether the user or patient respires, e.g., regularly respires, at least partly through the device. The respiration, e.g., regular respiration, of the user or patient at least partly through the device may include a plurality of inhalation and exhalation periods.

If it is detected by the sensor that the aerosol delivery device is not being used for an aerosol treatment or therapy, i.e., that the aerosol delivery device is not in use by a user or patient, the controller will deactivate or switch off the aerosol generator. The controller is configured so that, if no use of the aerosol delivery device for aerosol treatment or therapy is detected by the sensor, aerosol generation by the aerosol generator is stopped. The aerosol generator is thus deactivated or switched off by the controller if an interruption of the use of the aerosol delivery device for aerosol treatment is detected by the sensor.

Since, in the aerosol delivery device of the invention, the aerosol generator is deactivated, stopping aerosol generation by the aerosol generator, if the sensor detects that the device is not being used for aerosol treatment or therapy, aerosol losses inside and outside the device are significantly reduced. If the aerosol treatment is intentionally or unintentionally interrupted, e.g., by a distraction of the user or patient or a disturbance of the user's or patient's regular respiration, for example, due to a cough, a choke, a convulsion or the like, the aerosol generator can be quickly and reliably deactivated.

Indeterminable aerosol losses, which may otherwise be caused by such interruptions, are thus reliably prevented, allowing for the amount of aerosol delivered to the desired location within the user's or patient's body to be accurately determined. In this way, it can be ensured that the generated aerosol is efficiently supplied to the user or patient, thereby enabling a quick and efficient aerosol treatment or therapy with a precise and consistent aerosol dosage.

The controller may be connected to the sensor, in particular, to an output of the sensor. The controller may communicate with the sensor by wireless communication. The sensor may be configured to generate a detection signal indicating a use of the aerosol delivery device for aerosol treatment, i.e., indicating whether or not the aerosol delivery device is being used by a user or patient for an aerosol treatment. This detection signal may be transmitted to the controller, e.g., through an output of the sensor. The controller may be configured to deactivate the aerosol generator if the detection signal of the sensor indicates that the aerosol delivery device is not being used for an aerosol treatment or therapy.

The controller may be any type of controller, e.g., a controller unit, a controller element, a controller circuit or the like, which is capable of receiving an input, e.g., an input signal, from the sensor and controlling the aerosol generator based on this input.

The controller may be connected to the aerosol generator, e.g., to a power supply element of the aerosol generator. The controller may communicate with the aerosol generator by wireless communication.

The controller may be configured to deactivate or switch off the aerosol generator only if no use of the aerosol delivery device for aerosol treatment or therapy is detected by the sensor.

The sensor may be a mechanical and/or electric sensor. The sensor may be configured to sense a fluid flow, e.g., a fluid flow through the aerosol delivery device, a temperature, a temperature difference or gradient, a sound, a noise, an acoustic background, signal or effect, a pressure, a static or dynamic pressure difference or gradient, a vibration, an oscillation, a resistance, a conductivity, a force, an acceleration or the like or any combination thereof.

For example, the sensor may be configured to measure air flow through the device, e.g., by patients' breathing. Alternatively, the sensor may be formed as a force sensor, such as a bending beam sensor, for sensing the application of a force, a pressure detector or a microphone for detecting a pressure and/or pressure difference and/or pressure gradient and/or fluctuation (noise), a thermal sensor or a hot-wire or hot-film anemometer for detecting a temperature and/or temperature difference and/or temperature gradient, a resistance or conductivity sensor for detecting a resistance and/or conductivity, e.g., due to a contact of the aerosol delivery device with a user or patient, e.g., the skin of a user or patient, an acceleration sensor for detecting an acceleration and/or vibration and/or oscillation of the device or the like. The sensor may be formed as a combination of any of these elements.

The sensor may be configured to detect the use of the aerosol delivery device for aerosol treatment by sensing static or dynamic pressure differences, flow forces, electrical conductivity or acoustic or thermodynamic effects.

The aerosol delivery device may be an aerosol generation device, an aerosol inhalation device, a medical aerosol device, an aerosol diagnostic device, an aerosol prophylactic device, an aerosol therapeutic device, an aerosol humidification device, an aerosol therapy device or the like.

The aerosol generator may be a nebuliser, an atomiser, such as a humidifier, a pneumatic nebuliser, an electronic nebuliser, an ultrasonic nebuliser, an electro-hydrodynamic nebuliser, an electrostatic nebuliser, a membrane nebuliser, a vibrating membrane nebuliser, e.g., an electronic vibrating membrane nebuliser, a jet nebuliser, a humidifier-nebuliser for ventilation devices or the like.

In particular, the aerosol generator may be an electronic nebuliser, e.g., a piezo-electrically driven nebuliser, i.e., a nebuliser driven by a piezo-electric element. In this case, the aerosol generator can be deactivated by the controller in a particularly simple and reliable manner.

The aerosol generator may be a jet nebuliser employing pressurised air and/or a compressor, such as those disclosed in U.S. Pat. No. 5,957,389 andUS-A-2007/0068513, the contents of which are hereby incorporated herein by reference in their entirety.

The aerosol generator may be a vibrating membrane nebuliser, such as those disclosed in EP-A-2 030 644, US-A-2012/0085344 and US-A-2013/0112197, the contents of which are hereby incorporated herein by reference in their entirety.

A fluid to be nebulised or aerosolised by the aerosol generator may be a fluid for the generation of a pharmaceutical aerosol for the delivery of an active compound.

An active compound is a natural, biotechnology-derived or synthetic compound or mixture of compounds useful for the diagnosis, prevention, management, or treatment of a disease, condition, or symptom of an animal, in particular a human. Other terms which may be used as synonyms of active compound include, for example, active ingredient, active pharmaceutical ingredient, drug substance, diagnostic material, drug, medicament and the like. The fluid could be of a liquid, solution, suspension, colloidal mixture or liposomal formulation form and can be prepared, mixed or opened before or during the application.

The active compound comprised in the aerosol used for the device and the method of the invention may be a substance, drug or a medicament which is useful for the prevention, management, diagnosis or treatment of any disease, symptom, or condition affecting the body cavities, the abdomen, the eyes, the intestine, the stomach, the nose, the nasal cavities, the sinuses, and/or the osteomeatal complex, the mouth, the trachea, the lungs, the bronchi, the bronchioles, the alveoli and/or the respiratory tract.

In particular, an aerosol comprising an active compound which is useful for the prevention, management, diagnosis or treatment of any disease, symptom or condition affecting the paranasal sinuses may be generated and transported to the paranasal sinuses using an aerosol generator such as that disclosed in U.S. Pat. No. 7,980,247, the content of which is hereby incorporated herein by reference in its entirety.

Among the active compounds which may be useful for serving one of the purposes named previously and that may be used together with the present invention, are, for example, substances selected from the group consisting of anti-inflammatory compounds, anti-infective agents, antiseptics, prostaglandins, endothelin receptor agonists, phosphodiesterase inhibitors, beta-2-sympathicomimetics, decongestants, vasoconstrictors, anticholinergics, immunomodulators, mucolytics, anti-allergic drugs, antihistaminics, mast-cell stabilizing agents, tumor growth inhibitory agents, wound healing agents, local anaesthetics, antioxidants, oligonucleotides, peptides, proteins, vaccines, vitamins, plant extracts, cholinesterase inhibitors, vasoactive intestinal peptide, serotonin receptor antagonists, and heparins, glucocorticoids, anti-allergic drugs, antioxidants, vitamins, leucotriene antagonists, antibiotics, antifungals, antivirals, mucolytics, decongestants, antiseptics, cytostatics, immunomodulators, vaccines, wound healing agents, local anaesthetics, oligonucleotides, xanthin derived agents, peptides, proteins and plant extracts.

Such compound may be used in the form of a suspension, a solution, a colloidal formulation (i.e. liposomal), etc.

Examples of potentially useful anti-inflammatory compounds are glucocorticoids and non-steroidal anti-inflammatory agents such as betamethasone, beclomethasone, budesonide, ciclesonide, dexamethasone, desoxymethasone, fluocinolone acetonide, fluocinonide, flunisolide, fluticasone, icomethasone, rofleponide, triamcinolone acetonide, fluocortin butyl, hydrocortisone, hydroxycortisone-17-butyrate, prednicarbate, 6-methylprednisolone aceponate, mometasone furoate, dehydroepiandrosterone-sulfate (DHEAS), elastane, prostaglandin, leukotriene, bradykinin antagonists, non-steroidal anti-inflammatory drugs (NSAIDs), such as ibuprofen including any pharmaceutically acceptable salts, esters, isomers, stereoisomers, diastereomers, epimers, solvates or other hydrates, prodrugs, derivatives, or any other chemical or physical forms of active compounds comprising the respective active moieties.

Examples of anti-infective agents, whose class or therapeutic category is herein understood as comprising compounds which are effective against bacterial, fungal, and viral infections, i.e. encompassing the classes of antimicrobials, antibiotics, antifungals, antiseptics, and antivirals, are

- penicillins, including benzylpenicillins (penicillin-G-sodium, clemizone penicillin, benzathine penicillin G), phenoxypenicillins (penicillin V, propicillin), aminobenzylpenicillins (ampicillin, amoxycillin, bacampicillin), acylaminopenicillins (azlocillin, mezlocillin, piperacillin, apalcillin), carboxypenicillins (carbenicillin, ticarcillin, temocillin), isoxazolyl penicillins (oxacillin, cloxacillin, dicloxacillin, flucloxacillin), and amidine penicillins (mecillinam);
- cephalosporins, including cefazolins (cefazolin, cefazedone); cefuroximes (cefuroxim, cefamandole, cefotiam), cefoxitins (cefoxitin, cefotetan, latamoxef, flomoxef), cefotaximes (cefotaxime, ceftriaxone, ceftizoxime, cefmenoxime), ceftazidimes (ceftazidime, cefpirome, cefepime), cefalexins (cefalexin, cefaclor, cefadroxil, cefradine, loracarbef, cefprozil), and cefiximes (cefixime, cefpodoxim proxetile, cefuroxime axetil, cefetamet pivoxil, cefotiam hexetil), loracarbef, cefepim, clavulanic acid/amoxicillin, Ceftobiprole;
- synergists, including beta-lactamase inhibitors, such as clavulanic acid, sulbactam, and tazobactam;
- carbapenems, including imipenem, cilastin, meropenem, doripenem, tebipenem, ertapenem, ritipenam, and biapenem;
- monobactams, including aztreonam;
- aminoglycosides, such as apramycin, gentamicin, amikacin, isepamicin, arbekacin, tobramycin, netilmicin, spectinomycin, streptomycin, capreomycin, neomycin, paromoycin, and kanamycin;
- macrolides, including erythromycin, clarythromycin, roxithromycin, azithromycin, dithromycin, josamycin, spiramycin and telithromycin;
- gyrase inhibitors or fluroquinolones, including ciprofloxacin, gatifloxacin, norfloxacin, ofloxacin, levofloxacin, perfloxacin, lomefloxacin, fleroxacin, garenoxacin, clinafloxacin, sitafloxacin, prulifloxacin, olamufloxacin, caderofloxacin, gemifloxacin, balofloxacin, trovafloxacin, and moxifloxacin;
- tetracyclins, including tetracyclin, oxytetracyclin, rolitetracyclin, minocyclin, doxycycline, tigecycline and aminocycline;
- glycopeptides, inlcuding vancomycin, teicoplanin, ristocetin, avoparcin, oritavancin, ramoplanin, and peptide 4;
- polypeptides, including plectasin, dalbavancin, daptomycin, oritavancin, ramoplanin, dalbavancin, telavancin, bacitracin, tyrothricin, neomycin, kanamycin, mupirocin, paromomycin, polymyxin B and colistin;
- sulfonamides, including sulfadiazine, sulfamethoxazole, sulfalene, co-trimoxazole, co-trimetrol, co-trimoxazine, and co-tetraxazine;

azoles, including clotrimazole, oxiconazole, miconazole, ketoconazole, itraconazole, fluconazole, metronidazole, tinidazole, bifonazol, ravuconazol, posaconazol, voriconazole, and ornidazole and other antifungals including flucytosin, griseofulvin, tolnaftat, naftifin, terbinafin, amorolfin, ciclopiroxolamin, echinocandins, such as micafungin, caspofungin, anidulafungin;

nitrofurans, including nitrofurantoin and nitrofuranzone;

polyenes, including amphotericin B, natamycin, nystatin, flucocytosine, flucytosine;

other antibiotics, including tithromycin, lincomycin, clindamycin, oxazolidinones (linzezolids), ranbezolid, streptogramine A+B, pristinamycin A+B, Virginiamycin A+B, dalfopristin/quinupristin (Synercid), chloramphenicol, ethambutol, pyrazinamid, terizidon, dapson, prothionamid, fosfomycin, fucidinic acid, rifampicin, isoniazid, cycloserine, terizidone, ansamycin, lysostaphin, iclaprim, mirocin B17, clerocidin, filgrastim, and pentamidine;

antivirals, including aciclovir, ganciclovir, birivudin, valaciclovir, zidovudine, didanosin, thiacytidin, stavudin, lamivudin, zalcitabin, ribavirin, nevirapirin, delaviridin, trifluridin, ritonavir, saquinavir, indinavir, foscarnet, amantadin, podophyllotoxin, vidarabine, tromantadine, and proteinase inhibitors, si RNA based drugs;

antiseptics, including acridine derivatives, iodine-povidone, benzoates, rivanol, chlorhexidine, quarternary ammonium compounds, cetrimides, biphenylol, clorofene, taurolidine and octenidine;

plant extracts or ingredients, such as plant extracts from chamomile, *hamamelis, echinacea*, calendula, thymian, bromelain, papain, *pelargonium*, pine trees, essential oils, myrtol, pinen, limonen, cineole, thymol, mentol, camphor, tannin, alpha-hederin, bisabolol, lycopodin, vitapherole;

wound healing compounds including dexpantenol, allantoin, vitamins, hyaluronicacid, alpha-antitrypsin, anorganicandorganic zinc salts/compounds, salts of bismuth and selen;

interferones (alpha, beta, gamma), tumor necrosis factors, cytokines, interleukines;

immunmodulators including methotrexat, azathioprine, cyclosporine, tacrolimus, sirolimus, rapamycin, mofetil; mofetil-mycophenolate.

antibody (Ab), also known as an immunoglobulin (Ig), including immunoglobulin G (IgG), immunoglobulin A (IgA), immunoglobulin M (IgM) and/or immunoglobulin E (IgE); as well as fragments of antibodies, also known as Fab (fragment, antigen-binding) region, complementarity determining regions (CDRs), Fc (Fragment, crystallizable) region, or Fc receptors.

cytostatics and metastasis inhibitors;

alkylants, such as nimustine, melphanlane, carmustine, lomustine, cyclophosphosphamide, ifosfamide, trofosfamide, chlorambucil, busulfane, treosulfane, prednimustine, thiotepa;

antimetabolites, e.g. cytarabine, fluorouracil, methotrexate, mercaptopurine, tioguanine;

alkaloids, such as vinblastine, vincristine, vindesine;

antibiotics, suchasalcarubicine, bleomycine, dactinomycine, daunorubicine, doxorubicine, epirubicine, idarubicine, mitomycine, plicamycine;

complexes of transition group elements (e.g. Ti, Zr, V, Nb, Ta, Mo, W, Pt) such as carboplatinum, cis-platinum and metallocene compounds such as titanocendichloride;

amsacrine, dacarbazine, estramustine, etoposide, beraprost, hydroxycarbamide, mitoxanthrone, procarbazine, temiposide;

paclitaxel, gefitinib, vandetanib, erlotinib, iressa, zactima, poly-ADP-ribose-polymerase (PRAP) enzyme inhibitors, banoxantrone, gemcitabine, pemetrexed, bevacizumab, ranibizumab. Examples of potentially useful mucolytics are DNase (including dornasealpha), P2Y2-agonists(denufosol), drugs affecting chloride and sodium permeation, such as N-(3,5-Diamino-6-chloropyrazine-2-carbony)-N'-{4-[4-(2,3-dihydroxypropoxy)-phenyl]butyl}guanidine methanesulfonate (PARION 552-02), heparinoids, guaifenesin, acetylcysteine, carbocysteine, ambroxol, bromhexine, tyloxapol, lecithins, myrtol, and recombinant surfactant proteins.

Examples of potentially useful vasoconstrictors and decongestants which may be useful to reduce the swelling of the mucosa are phenylephrine, naphazoline, tramazoline, tetryzoline, oxymetazoline, fenoxazoline, xylometazoline, epinephrine, isoprenaline, hexoprenaline, and ephedrine.

Examples of potentially useful local anaesthetic agents include benzocaine, tetracaine, procaine, lidocaine and bupivacaine.

Examples of potentially useful antiallergic agents include the afore-mentioned glucocorticoids, cromolyn sodium, nedocromil, cetrizin, loratidin, montelukast, roflumilast, ziluton, omalizumab, heparinoids and other antihistamins, including azelastine, cetirizin, desloratadin, ebastin, fexofenadin, levocetirizin, loratadin.

Examples of potentially useful anticholinergic agents include ipratropium bromide, tiotropium bromide, oxitropium bromide, glycopyrrolate.

Examples of potentially useful beta-2-sympathicomimetic agents include salbutamol, fenoterol, formoterol, indacaterol, isoproterenol, metaproterenol, salmeterol, terbutaline, clenbuterol, isoetarine, pirbuterol, procaterol, ritodrine.

Examples of xanthine derived agents include theophylline, theobromine, caffeine.

Antisense oligonucleotides are short synthetic strands of DNA (or analogs) that are complimentary or antisense to a target sequence (DNA, RNA) designed to halt a biological event, such as transcription, translation or splicing. The resulting inhibition of gene expression makes oligonucleotides dependent on their composition useful for the treatment of many diseases and various compounds are currently clinically evaluated, such as ALN-RSV01 to treat the respiratory syncytical virus by, AVE-7279 to treat asthma and allergies, TPI-ASM8 to treat allergic asthma, 1018-ISS to treat cancer.

Also si RNA can be applied as an active compound.

Examples of potentially useful peptides and proteins include antibodies against toxins produced by microorganisms, antimicrobial peptides such as cecropins, defensins, thionins, and cathelicidins.

The controller may be configured to activate the aerosol generator if the use of the aerosol delivery device for aerosol treatment is detected by the sensor. The controller may thus be configured to activate the aerosol generator if it is detected by the sensor that the aerosol delivery device is being used for an aerosol treatment or aerosol therapy, e.g., by a user or patient. Hence, if there has been an interruption in the aerosol treatment or therapy, it can be ensured that the treatment is resumed in a quick, reliable and efficient manner after the interruption, so that the loss of time caused by the interruption can be kept to a minimum. In this way, the efficiency of the aerosol treatment or therapy can be further improved.

The aerosol generator may be a continuous aerosol generator, e.g., a continuously operating nebuliser. A continuous aerosol generator is configured to continuously generate an aerosol, e.g., during the operation of the aerosol delivery device and/or the aerosol treatment or therapy. Such a continuous aerosol generator provides the advantages of a simple structure and a quick administration of a desired aerosol dosage. The sensor and the controller of the aerosol delivery device of the invention allow for the continuous aerosol generator to be operated with a minimum amount or degree of aerosol loss.

The controller may be configured to activate the aerosol generator so as to operate in a continuous mode if the use of the aerosol delivery device for aerosol treatment is detected by the sensor. Herein, the term "continuous mode" refers to a mode of operation of the aerosol generator, in which the aerosol generator continuously generates an aerosol.

In one embodiment, the sensor is configured to detect the use of the aerosol delivery device for aerosol treatment by sensing the presence of a user's or patient's respiration through the aerosol delivery device. In particular, the sensor may be configured to detect the use of the aerosol delivery device for aerosol treatment by sensing the presence of a user's or patient's regular respiration through the aerosol delivery device.

In this way, an interruption or irregularity in the user's or patient's respiration through the aerosol delivery device, e.g., induced by a cough, a choke, a convulsion or the like, can be reliably identified and the aerosol generator can be accordingly deactivated by the controller. Thus, any interruption of the aerosol treatment can be determined in a quick and reliable manner, allowing for a particularly efficient aerosol treatment with a high aerosol dosage precision and consistency.

For sensing the presence of a user's or patient's respiration, in particular, a user's or patient's regular respiration, through the aerosol delivery device, the sensor may be configured to sense a fluid flow, e.g., breathing air flow, through the device and/or a pressure difference, pressure drop or pressure fluctuation and/or a temperature or temperature gradient in the device and/or an acoustic level, such as a sound or noise level, in the device or the like.

During the use of the aerosol delivery device a patient's respiration may be detected by a sensor used for measurement of the presence or non-presence of a pressure, pressure difference and/or flow or fluctuation of the pressure, pressure difference and/or flow, for example in a range, relevant or characteristic for use versus non-use of the device, as detected by the sensor, for example flow sensor, pressure sensor or pressure difference sensor mentioned above.

The sensor may be configured to detect that the aerosol delivery device is not being used for aerosol treatment or therapy only if no respiration, e.g., no regular respiration, of a user or patient through the aerosol delivery device is sensed by the sensor. In this case, the aerosol generator is deactivated by the controller only if no respiration, e.g., regular respiration, of a user or patient through the aerosol delivery device is sensed by the sensor. Thus, no deactivation of the aerosol generator is carried out, if the presence of a user's or patient's respiration, e.g., regular respiration, including inhalation and exhalation, through the device is sensed by the sensor. In this way, it can be ensured that the aerosol generator is deactivated only if an interruption of the aerosol treatment occurs.

In one embodiment, the sensor is configured to detect the use of the aerosol delivery device for aerosol treatment by sensing a contact between the aerosol delivery device and a user or patient, e.g., a user's or patient's skin. In particular, the sensor may be configured to detect the use of the aerosol delivery device for aerosol treatment by sensing a contact between the device and a user's or patient's hand or hands and/or lips and/or nose. In this way, it can be quickly and reliably determined if the user or patient has removed the aerosol delivery device, e.g., from his lips and/or nose, and/or released, e.g., put down, the aerosol delivery device, thereby interrupting the aerosol treatment.

For sensing a contact between the aerosol delivery device and a user or patient, the sensor may be, for example, configured as a resistance or conductivity sensor, e.g., arranged to measure the resistance or conductivity of the user's or patient's skin in contact with the device. Further, the sensor may be configured as a force and/or pressure sensor, sensing a force or pressure applied to the aerosol generation device by the user's or patient's hand or hands and/or lips and/or nose or the like. Thus, an interruption of the aerosol treatment can be detected in a particularly reliable manner.

The controller may be configured to operate the aerosol generator in a pulsed mode after deactivation of the aerosol generator. Herein, the term "pulsed mode" refers to a mode of operation of the aerosol generator in which the aerosol generator is cyclically or periodically switched on and off by the controller, so as to generate a plurality of aerosol generation pulses, i.e., aerosol pulses. This is done in a way to periodically re-fill the mixing chamber after deactivation of the aerosol generator during the pulsed mode in an "on" phase and at the same time reduce aerosol losses by deactivation of the aerosol generator in an "off" phase.

These aerosol generation pulses may be provided at regular or irregular time intervals, e.g., in the range of 0.001 s to 10 s, preferably in the range of 0.01 s to 5 s, and more preferably in the range of 0.5 s to 3 s. In an embodiment, the regular time intervals are in the range of 50 ms to 2000 ms, preferably 100 ms to 1500 ms and more preferably 200 ms to 1000 ms.

The aerosol generation pulses may have the same or different pulse durations. The pulse duration or durations may be in the range of 0.001 s to 10 s, preferably in the range of 0.01 s to 5 s and, more preferably in the range of 0.5 s to 3 s. In an embodiment, the regular time intervals are in the range of 50 ms to 2000 ms, preferably 100 ms to 1500 ms and more preferably 200 ms to 1000 ms.

The aerosol generator pulses in which the aerosol generator is cyclically or periodically switched "on" and "off" by the controller may be in the range of 0.01 s to 1 s "on" versus 1 s to 10 s "off" and, more preferably 0.05 s to 0.5 s "on" versus 1 s to 5 s "off" and, even more preferably 0.1 s to 0.5 s "on" versus 1 s to 3 s "off". In an embodiment, the aerosol generator pulses in which the aerosol generator is cyclically or periodically switched "on" and "off" by the controller may be less than or equal to 2 s "on" versus less than or equal to 10 s "off" and, more preferably less than or equal to 1 s "on" versus less than or equal to 5 s "off" and, even more preferably less than or equal to 0.5 s "on" versus less than or equal to 3 s "off".

By operating the aerosol generator in the pulsed mode, an indication is provided to the user or patient that the aerosol delivery device is in a fully functional or operable state. The aerosol losses caused by this pulsed mode are negligibly small as compared to a continuous aerosol generation during an interruption of the aerosol treatment or therapy.

Moreover, the aerosol generation pulses generated during the interruption of the aerosol treatment may serve to fill a mixing chamber or aerosol chamber of the aerosol delivery device with aerosol, in order to ensure that a sufficient amount of aerosol is provided in the mixing chamber or aerosol chamber for the first breath of the next aerosol inhalation cycle, before the aerosol generator is activated. In this way, the pulsed mode enables a quick and smooth resumption of the aerosol treatment after an interruption without any delay. Hence, the aerosol treatment can be performed in a particularly quick and efficient manner.

The controller may be configured to deactivate the aerosol generator if no use of the aerosol delivery device for aerosol treatment is detected by the sensor, subsequently operate the aerosol generator in a pulsed mode until a use of the aerosol delivery device for aerosol treatment is detected by the sensor and, if such a use is detected by the sensor, activate the aerosol generator, e.g., activate the aerosol generator so as to run in a continuous mode, continuously generating aerosol.

The controller may be configured to operate the aerosol generator in a pulsed mode if no use of the aerosol delivery device for aerosol treatment is detected by the sensor and subsequently deactivate the aerosol generator, e.g., after a period of time, e.g., a first period of time, in which no use of the aerosol delivery device for aerosol treatment has been detected by the sensor. Further, the controller may be configured to fully deactivate the aerosol delivery device after a second period of time, in which no use of the aerosol delivery device for aerosol treatment has been detected by the sensor, wherein the second period of time is longer than the first period of time. If the aerosol delivery device is fully deactivated after the second period of time, a warning function could be activated, e.g., by the controller, indicating to an operator, user or patient that the aerosol therapy had not been completed. For example, a warning message could be displayed on a display of the aerosol delivery device or a warning sound signal could be emitted, e.g., by the aerosol delivery device.

The aerosol delivery device may further comprise a monitoring unit or monitoring element configured to monitor an operating ability or functional state of the aerosol generator. The monitoring unit or element may be configured to provide a visible error message, e.g., by an LED or a display, and/or an audible error message, e.g., using a beeper or the like, to a user or patient if the aerosol generator is not in a functional or operable state. In particular, the monitoring unit or element may be configured to monitor whether the aerosol generator is undamaged and/or whether there is a sufficient amount of fluid to be nebulised in contact with the aerosol generator.

In this way, an interruption caused by a failure of the aerosol generator or a shortage in the fluid supply can be reliably distinguished from an interruption of the aerosol treatment caused on the side of the user or patient.

The monitoring unit or element may form part of the controller. The monitoring unit or element may be provided as a separate element. The aerosol generator may be a vibrating membrane nebuliser, e.g., a vibrating membrane nebuliser with a mixing chamber or aerosol chamber. The sensor and the controller of the aerosol delivery device of the invention can be particularly advantageously used in combination with a vibrating membrane nebuliser, in particular, a vibrating membrane nebuliser with a mixing chamber or aerosol chamber. In this case, a quick administration of an aerosol with a reproducible high efficiency and a consistent aerosol dosage can be achieved in a particularly simple manner. Aerosol losses caused by intentional or unintentional interruptions of the aerosol treatment are reliably prevented by the sensor and the controller. The controller may be configured to deactivate the aerosol generator immediately upon detection by the sensor that the aerosol delivery device is not being used for aerosol treatment. Herein, the term "immediately" defines that the controller is configured to deactivate the aerosol generator as soon as it is notified or informed by the sensor that the aerosol delivery device is not being used for aerosol treatment. In this case, the controller is configured to deactivate the aerosol generator without any delay, e.g., any artificial delay, which extends beyond the time, i.e., the regular time, required by the controller to carry out the deactivation process. In this way, aerosol losses during an intentional or unintentional interruption of the aerosol treatment can be minimised.

The controller may be configured to deactivate the aerosol generator after the lapse of a period of time, e.g., a preset or predetermined period of time, if no use of the aerosol delivery device for aerosol treatment is detected by the sensor. The period of time may be in the range of 0.5 s to 20 s, preferably in the range of 1 s to 15 s, more preferably in the range of 2 s to 10 s and even more preferably in the range of 3 s to 5 s. In an embodiment, the period of time may be in the range of 0.1 s to 10 min, preferably in the range of 1 s to 5 min, more preferably in the range of 2 s to 1 min and even more preferably in the range of 3 s to 30 s. The period of time may, for example, start with the beginning of an exhalation period or step of a user or patient, or with the point of time in which no use of the aerosol delivery device for aerosol treatment is detected by the sensor, e.g., by sensing the absence of a user's or patient's respiration, e.g., regular respiration, through the aerosol delivery device and/or sensing a lack of contact between the aerosol delivery device and the user or patient.

By choosing the period of time after which the aerosol generator is deactivated in the manner specified above, e.g., by selecting a period of time in the range of 0.5 s to 20 s, preferably 1 s to 15 s, more preferably 2 s to 10 s and even more preferably 3 s to 5 s, the sensitivity of the deactivation is advantageously adjusted.

If the aerosol generator is deactivated too early, no sufficient amount of aerosol may be provided in the aerosol delivery device for a user's or patient's possible next inhalation. On the other hand, if the aerosol generator is deactivated after a period of time, such as one of those specified above, the aerosol generator keeps generating aerosol for part of the time in which no use of the aerosol delivery device for aerosol treatment is detected by the sensor. In this way, it can be ensured that a sufficient amount of aerosol, or even an aerosol bolus, is provided for the next inhalation.

If the aerosol generator is deactivated too late, aerosol losses may be increased, thus impairing the aerosol dosage accuracy and efficiency.

For example, the controller may be configured to deactivate the aerosol generator after the lapse of a period of time of 4 s to 6 s after the beginning of an exhalation period or step of a user or patient, or if no use of the aerosol delivery device for aerosol treatment is detected by the sensor. Further, the controller may be configured to deactivate the aerosol generator after the lapse of a period of time of 2 s to 3 s after it has been detected by the sensor that the aerosol delivery device is not being used for aerosol treatment.

Moreover, the controller may be configured to fully deactivate the aerosol delivery device after the lapse of a period of time of 3 min to 10 min after it has been detected by the sensor that the aerosol delivery device is not being used for aerosol treatment. In this way, the aerosol delivery device can be operated in a particularly energy and cost efficient manner. If the aerosol delivery device is fully deactivated after the lapse of this period of time, a warning function could be activated, e.g., by the controller, indicating to an operator, user or patient that the aerosol therapy had not been completed. For example, a warning message could be displayed on a display of the aerosol delivery device or a warning sound signal could be emitted, e.g., by the aerosol delivery device.

The invention further provides a method for operating an aerosol delivery device, comprising the steps of operating an aerosol generator for generating an aerosol in the aerosol delivery device, detecting a use of the aerosol delivery device for aerosol treatment by means of a sensor, and deactivating the aerosol generator by means of a controller if no use of the aerosol delivery device for aerosol treatment is detected by the sensor.

The aerosol generator may be automatically deactivated by means of the controller if no use of the aerosol delivery device for aerosol treatment is detected by the sensor. Herein, the term "automatically" defines that no external action, i.e., no action by a user or patient, is required for the aerosol generator to be deactivated. For example, the controller may receive a detection signal from the sensor, indicating that the aerosol delivery device is not being used for an aerosol treatment or therapy, and deactivate the aerosol generator in response to this signal.

The method of the invention provides the advantageous effects already described in detail above for the device of the invention. In particular, the method enables a quick and efficient aerosol treatment in a simple manner.

The method may further comprise the step of activating the aerosol generator by means of the controller if the use of the aerosol delivery device for aerosol treatment is detected by the sensor.

The aerosol generator may be automatically activated by means of the controller if the use of the aerosol delivery device for aerosol treatment is detected by the sensor.

The aerosol generator may be a continuous aerosol generator, e.g., a continuously operated nebuliser. In particular, the aerosol generator may be a vibrating membrane nebuliser, e.g., a vibrating membrane nebuliser with a mixing chamber or aerosol chamber.

The use of the aerosol delivery device for aerosol treatment may be detected by sensing the presence of a user's or patient's respiration, e.g., regular respiration, through the aerosol delivery device.

The use of the aerosol delivery device for aerosol treatment may be detected by sensing a contact between the aerosol delivery device and a user or patient.

The method may further comprise the step of operating the aerosol generator in a pulsed mode after deactivation of the aerosol generator.

The method may further comprise a step of monitoring an operating ability or functional state of the aerosol generator by means of a monitoring unit or a monitoring element.

The aerosol generator may be deactivated after the lapse of a period of time if no use of the aerosol delivery device for aerosol treatment is detected by the sensor.

The method of the invention is a method for operating the aerosol delivery device of the invention. Hence, the further features disclosed in connection with the above description of the device of the invention may also be applied to the method of the invention.

BRIEF DESCRIPTION OF THE DRAWINGS

Hereinafter, non-limiting examples of the invention are explained with reference to the drawings, in which.

DETAILED DESCRIPTION OF CURRENTLY PREFERRED EMBODIMENTS

Figure 1:
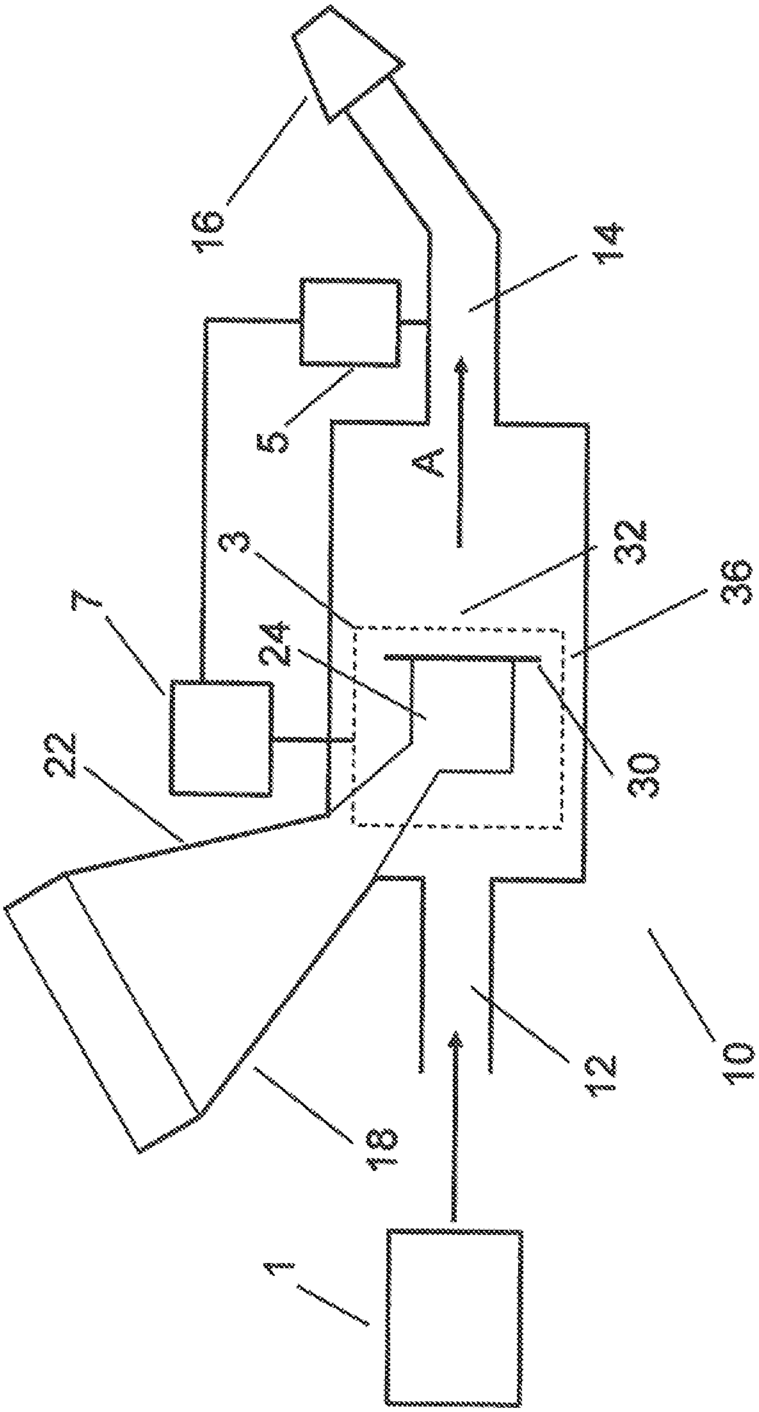
FIG. 1 shows a schematic longitudinally cut cross-sectional view of an aerosol delivery device according to an embodiment of the present invention.

FIG. 1 shows a schematic longitudinally cut cross-sectional view of an aerosol delivery device 10 according to a currently preferred embodiment of the present invention.

The aerosol delivery device 10 comprises an aerosol generator 3, which is a vibrating membrane nebuliser, an air inlet 12 for connection with a gas compressor 1 as a source of compressed air, and an adaptation element 14 that is equipped with a mouthpiece (not shown) 16 or optional nasal prongs (not shown) or an optional face mask (not shown) or an optional nosepiece (16) for adaptation to or communication with a user's or patient's respiratory system, nasal cavity etc.

Alternatively, the air inlet 12 may be an open and free air inlet, e.g., allowing for the introduction or entrainment of ambient air into the aerosol delivery device 10.

A fluid container 18 for receiving a fluid to be aerosolised or nebulised is disposed between the air inlet 12 and the adaptation element 14. The fluid container 18 is preferably integrally formed with the body of the aerosol delivery device 10 but, in further embodiments, may be configured such that it is partly or fully detachable from the body.

The body of the aerosol delivery device 10 is preferably made of plastic and preferably manufactured by an injection moulding process. The fluid container 18 may be designed so that it does not directly receive the fluid but rather has an opening element, such as a thorn, a spike, a hollow needle or the like, arranged on its inside that opens a fluid containing vessel, e.g., a vial, a blister, an ampoule, a container, a canister, a reservoir, a cartridge, a pot, a tank, a pen, a storage, a syringe or the like, inserted therein.

In general, any fluid to be aerosolised or nebulised may be received in the fluid container 18 and used for the generation of an aerosol in the aerosol delivery device 10, depending on the condition, diagnosis to be measured or disease to be treated or managed. The fluid composition may comprise one or more active compounds, as has been detailed above.

In the embodiment shown in FIG. 1, the one end of the fluid container 18 can be securely and tightly closed, for example, with a screw cap (not shown). At its other end, opposite the screw cap or the like, the fluid container 18 may have a tapered portion 22 that tapers towards a fluid chamber 24 of the aerosol generator 3. The fluid chamber 24 may be sealed by a sealing lip (not shown) or the like that forms a part of the chamber 24 and is tightly pressed against a membrane 30. The membrane 30 is provided with a plurality of minute openings or holes with diameters in the micrometer range that perforate the membrane 30.

Alternatively, the aerosol delivery device 10 may be configured without the fluid chamber 24. In this case, the fluid container 18 is arranged so that it abuts directly against the membrane 30. Thus, in this configuration, the tapered portion 22 tapers towards the membrane 30.

The membrane 30 can be vibrated or oscillated, for example, with the use of a piezo-electric element (not shown), such that the direction of the vibration is substantially perpendicular to the plane of the membrane 30. A controller 7 configured to supply electrical power to the aerosol generator 3 and to activate and deactivate the aerosol generator 3 is connected to the aerosol generator 3.

By inducing such vibrations of the membrane 30, fluid contained in the fluid chamber 24 is passed through the minute openings or holes of the membrane 30 and nebulised into a mixing chamber 32, e.g., an aerosol chamber or a nebuliser chamber, formed at the other side of the membrane 30 opposite to the fluid chamber 24, thereby generating an aerosol in the aerosol delivery device 10. In this way, the fluid chamber 24 and the membrane 30 together forma vibrating membrane nebuliser, i.e., the aerosol generator 3. A detailed description of this concept is presented, for example, in U.S. Pat. No. 5,518,179.

The aerosol generator 3 is a continuously operated nebuliser, continuously generating an aerosol in the aerosol delivery device 10 during the operation of the device 10.

The controller 7 comprises a computer and a control element (not shown), such as a transistor, that is connected to the membrane 30 for stopping and starting the membrane vibration and hence the aerosol generation by the aerosol generator 3.

A flow passage 36 is formed between the membrane 30 and the body of the aerosol delivery device 10 which allows for the passage of a gas, i.e., air in the present embodiment, supplied from the compressor 1 through the air inlet 12 and/or entrained by the patient's respiration through the air inlet 12.

Further, the aerosol delivery device 10 comprises a sensor 5 configured to detect a use of the aerosol delivery device 10 for aerosol treatment by sensing the presence of a patient's respiration through the aerosol delivery device 10, in particular, through the adaptation element 14. The sensor 5 is connected to the controller 7 and transmits a detection signal to the controller 7, indicating whether or not the aerosol delivery device 10 is being used for aerosol treatment, i.e., whether or not the user's or patient's respiration through the aerosol delivery device 10 is present.

The controller 7 is configured to deactivate the aerosol generator 3 if no use of the aerosol delivery device 10 for aerosol treatment is detected by the sensor 5 and to activate the aerosol generator 3 if the use of the aerosol delivery device 10 for aerosol treatment is detected by the sensor 5.

For example, the sensor 5 may be configured as a flow sensor for sensing a fluid flow through the device and/or a temperature sensor for sensing a temperature or temperature gradient in the device and/or an acoustic sensor, e.g., a sound sensor, for sensing an acoustic level, such as a sound or noise level, in the device and/or a pressure sensor detecting pressure differences, pressure drop or pressure fluctuations during use of the device.

The controller 7 may be configured to operate the aerosol generator 3 in a pulsed mode after deactivation of the aerosol generator 3.

In the following, two different examples of the operation of the aerosol delivery device 10 shown in FIG. 1, using two different configurations of the controller 7, will be explained with reference to FIGS. 1 and 2.

Figure 2:
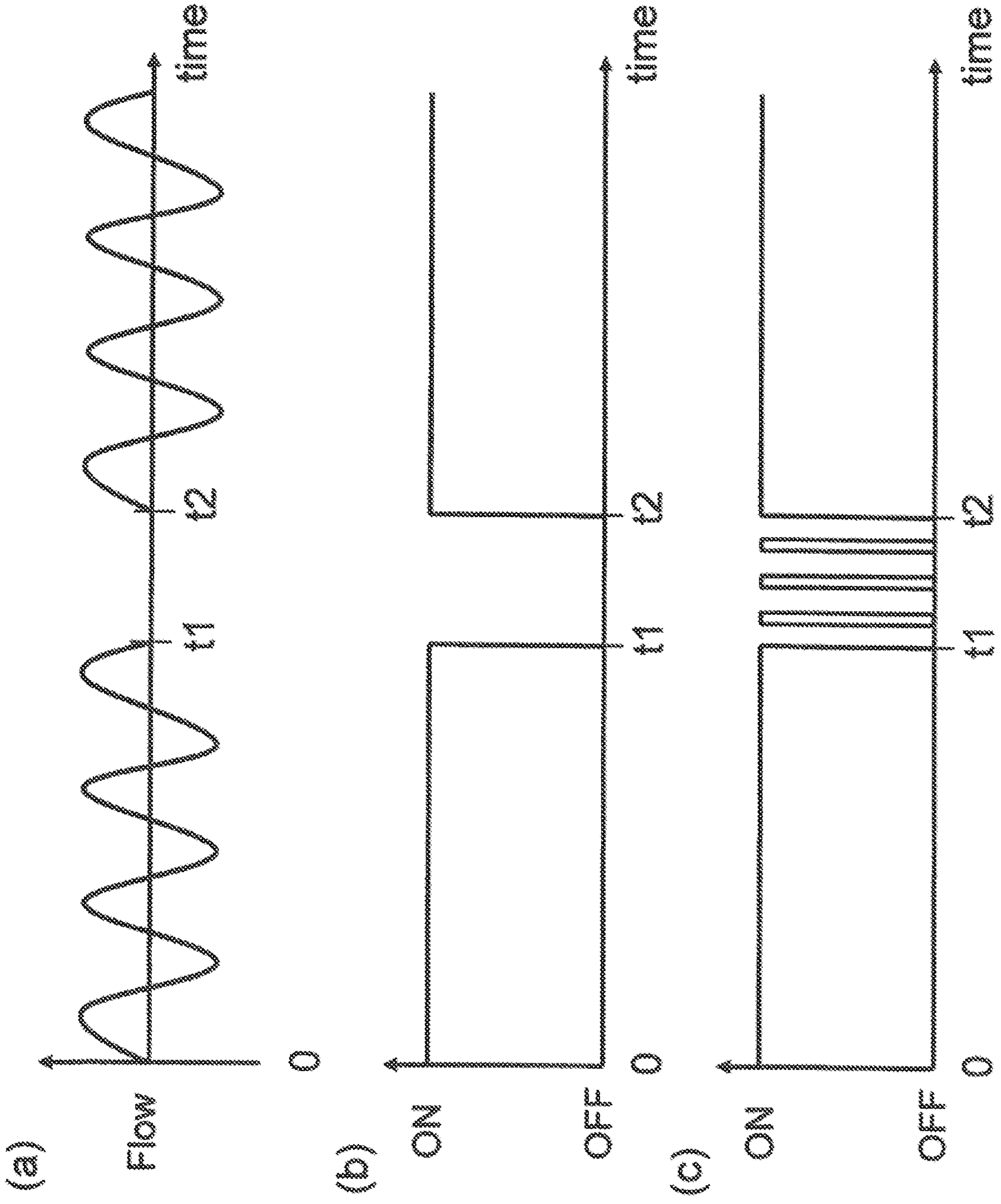
FIGS. 2(*a*)-(*c*) show schematic diagrams of operating modes of the aerosol delivery device shown in FIG. 1, wherein FIG. 2(*a*) shows an interrupted respiration pattern of a patient, FIG. 2(*b*) shows a first operating mode of the aerosol delivery device and FIG. 2(*c*) shows a second operating mode of the aerosol delivery device.

FIG. 2(*a*) shows a schematic diagram of the gas flow, i.e., air flow, through the adaptation element 14 for an interrupted regular respiration pattern of a user or patient, respiring through the aerosol delivery device 10. As can be seen from FIG. 2(*a*), the respiration pattern includes regular respiration, including inhalation and exhalation periods, through the aerosol delivery device 10 in the time interval from 0 to t1, an interruption of the respiration through the device 10 in the time interval from t1 to t2, e.g., due to the user or patient removing the nose piece (16), face mask (not shown), or mouthpiece (not shown) from his mouth, or face, or nose, and regular respiration, including inhalation and exhalation periods, through the device 10 in the time interval starting from t2.

FIGS. 2(*b*) and (*c*) show schematic diagrams of two different modes of operating the aerosol delivery device 10 of FIG. 1, using two different configurations of the controller 7, wherein FIG. 2(*b*) shows a continuous operation mode with subsequent permanent shut-off in the interruption period and FIG. 2(*c*) shows a pulsed operation mode in the interruption period.

In order to perform an aerosol treatment using the aerosol delivery device 10 schematically shown in FIG. 1, the fluid container 18 is first filled, for example, with 2 ml of an aerosolisable fluid that comprises an active compound, such as an antibiotic drug or the like, and tightly sealed with the screw cap (not shown). Then, the mouthpiece (not shown), a face mask (not shown) or a nose piece (16), of the adaptation element 14 is inserted into the nose, on the face or into the mouth of a user or patient having a medical condition to be treated.

The user or patient starts breathing through the mouthpiece (not shown), a face mask (not shown) or a nose piece (16), thereby inducing an air flow or pressure drop in the adaptation element 14. This air flow or pressure drop is sensed by the sensor 5. The sensor 5 thus generates a detection signal, indicating that the aerosol delivery device 10 is being used for aerosol treatment, and transmits this signal to the controller 7. In response to this signal, the controller 7 activates the aerosol generator 3 in order to generate an aerosol in the aerosol delivery device 10.

The aerosol generation by the aerosol generator 3 is started by vibrating or oscillating the membrane 30 so that it continuously nebulises or aerosolises the fluid supplied from the fluid container 18 and received in the fluid chamber 24 into the mixing chamber 32, so that the aerosol thus generated is made available for a user or patient and may be inhaled from the mixing chamber 32 via the mouthpiece (not shown), a face mask (not shown) or a nose piece (16), like nasal prongs. At the same time, a constant transport flow of gas, i.e., air in this embodiment, may be supplied, for example, at a flow rate of 0.5 to 5 L/min, preferably at a flow rate of 0.5 to 3 L/min, by the gas compressor 1.

Alternatively, as has been detailed above, the aerosol delivery device 10 may be configured without the fluid chamber 24. In this case, the fluid container 18 is arranged so that it abuts directly against the membrane 30 and the vibrating or oscillating membrane 30 directly nebulises or aerosolises the fluid supplied from the fluid container 18.

As is shown in FIG. 1, the plane of the membrane 30 is substantially perpendicular to the direction of aerosol transport (direction of arrow A in FIG. 1) towards the adaptation element 14, so that the risk of any aerosol loss at the walls of the aerosol delivery device 10 due to impaction is minimised. The air supplied by the compressor 1 and/or the air entrained via the air inlet 12 flows around the membrane 30 through the flow passage 36 and mixes with the nebulised or aerosolised fluid in the mixing chamber 32.

At the point of time t1, the respiration of the user or patient through the aerosol delivery device 10, i.e., the aerosol treatment, is interrupted, as is schematically shown in FIG. 2(*a*). At this point of time, the sensor 5 senses that no respiration through the aerosol delivery device 10 is present and generates a detection signal, indicating that the aerosol delivery device 10 is not being used for aerosol treatment by the user or patient. This detection signal is transmitted to the controller 7. In response to this signal, the controller 7 deactivates the aerosol generator 3, thus stopping the generation of aerosol in the aerosol generator 3, as is schematically shown in FIGS. 2(*b*) and (*c*).

At the point of time t2, the sensor 5 senses the presence of the user's or patient's respiration through the aerosol delivery device 10 and generates a detection signal, indicating that the aerosol delivery device 10 is being used for aerosol treatment. This detection signal is transmitted to the controller 7. In response to this signal, the controller 7 activates the aerosol generator 3, in order to start the continuous generation of aerosol in the aerosol generator 3, as is schematically shown in FIGS. 2(*b*) and (*c*).

In the embodiment shown in FIG. 2(*b*), the controller 7 is configured to deactivate the aerosol generator 3 if no use of the aerosol delivery device 10 for aerosol treatment is detected by the sensor 5 and to activate the aerosol generator 3 only if the use of the aerosol delivery device 10 for aerosol treatment is detected by the sensor 5. During the interruption of the aerosol treatment, i.e., in the time interval from t1 to t2, the aerosol generator 3 remains permanently switched off or deactivated, so that no aerosol is generated in the aerosol delivery device 10, as is schematically shown in FIG. 2(*b*). In this way, aerosol losses during the interruption of the aerosol treatment can be minimised.

In the embodiment shown in FIG. 2(*c*), the controller 7 is configured to deactivate the aerosol generator 3 if no use of the aerosol delivery device 10 for aerosol treatment is detected by the sensor 5, to operate the aerosol generator 3 in a pulsed mode after deactivation of the aerosol generator 3 and to activate the aerosol generator 3 so as to continuously generate aerosol if the use of the aerosol delivery device 10 for aerosol treatment is detected by the sensor 5. Hence, the controller 7 is configured to operate the aerosol generator 3 in the pulsed mode during the interruption of the aerosol treatment, i.e., in the time interval from t1 to t2.

In this way, the mixing chamber 32 is filled with aerosol during the interruption of the aerosol treatment, so that it can be ensured that a sufficient amount of aerosol is present in the mixing chamber 32 for the subsequent aerosol inhalation starting at the point of time t2. Moreover, the operation of the aerosol generator 3 in the pulsed mode indicates to the user or patient that the aerosol delivery device 10 is in a fully functional or operable state.

The pulses in the pulsed mode are spaced at regular time intervals in the range of 0.01 s to 5 s, more preferably in the range of 0.5 s to 5 s or, even more preferably in the range of 1 s to 3 s. In an embodiment, the regular time intervals are in the range of 0.1 s to 3 s or, even more preferably in the range of 0.3 s to 2 s. All of the pulses have the same pulse duration which lies in the range of 10 ms to 3000 ms or, more preferably in the range of 100 ms to 2000 ms or, even more preferably in the range of 300 ms to 1000 ms. Thus, the aerosol losses induced by the operation of the aerosol generator 3 in the pulsed mode are minimised and re-filling of the mixing chamber with aerosol for the continuation of the aerosol treatment is secured.

In the embodiments shown in FIGS. 2(*b*) and (*c*), the controller 7 is configured to deactivate the aerosol generator 3 immediately upon detection that the aerosol delivery device 10 is not being used for aerosol treatment. However, in other embodiments, the controller 7 may be configured to deactivate the aerosol generator 3 after the lapse of a period of time, e.g., a preset or predetermined period of time, if no use of the aerosol delivery device 10 for aerosol treatment is detected by the sensor 5, as has been detailed above.

This period of time may, for example, start from the beginning of the last exhalation period of the patient before the interruption of the aerosol treatment or from the detection of the interruption of the aerosol treatment, i.e., the point of time t1. In this case, the aerosol generator 3 is not deactivated at the point of time t1, as shown in FIGS. 2(*b*) and (*c*), but at a later point of time between t1 and t2.

While the aerosol generator 3 of the embodiment shown in FIG. 1 is a vibrating membrane nebuliser, any type of aerosol generator may be used for the aerosol delivery device of the present invention, as has been detailed above. The aerosol generator may be a nebuliser, an atomiser, such as a humidifier, a pneumatic nebuliser, an electronic nebuliser, an ultrasonic nebuliser, an electro-hydrodynamic nebuliser, an electrostatic nebuliser, a jet nebuliser, a humidifier-nebuliser for ventilation devices or the like.

In particular, the aerosol generator may be a jet nebuliser employing pressurised air and/or a compressor, such as those disclosed in U.S. Pat. No. 5,957,389, US-A-2007/0068513, DE-A-100 22 795 and DE-A-102 26 334.

Further, while the aerosol delivery device 10 of the embodiment shown in FIG. 1 comprises a nose piece (16), face mask (not shown) or mouthpiece (not shown) for adaptation to or communication with a user's or patient's nose, face or mouth, the aerosol delivery device of the present invention may comprise nasal prongs, a nosepiece or a face mask, e.g., for adaptation to or communication with a user's or patient's body cavities, abdomen, eyes, intestine, stomach, nose, nasal cavities, sinuses, osteomeatal complex, trachea, lungs, bronchi, bronchioles, alveoli and/or respiratory tract.

In particular, an aerosol comprising an active compound which is useful for the prevention, management, diagnosis or treatment of any disease, symptom or condition affecting the paranasal sinuses may be generated and transported to the paranasal sinuses using an aerosol delivery device comprising a nosepiece and an aerosol generator such as that disclosed in U.S. Pat. No. 7,980,247.

The invention claimed is:

1. An aerosol delivery device comprising:

an aerosol generator for generating which generates an aerosol in the aerosol delivery device, a sensor which detects a use of the aerosol delivery device for aerosol treatment, and a controller which deactivates the aerosol generator if no use of the aerosol delivery device for aerosol treatment is detected by the sensor, wherein the controller deactivates the aerosol generator after the lapse of a period of time if no use of the aerosol delivery device for aerosol treatment is detected by the sensor, wherein the sensor detects the use of the aerosol delivery device for aerosol treatment by sensing a user's regular respiration, including both inhalation and exhalation, through the aerosol delivery device, and wherein the aerosol generator is a vibrating membrane nebulizer.

2. The aerosol delivery device according to claim 1, wherein the period of time is in a range of 1 s to 5 min.

3. The aerosol delivery device according to claim 1, wherein the aerosol generator is a continuous aerosol generator, and the aerosol generator continuously generates the aerosol during aerosol treatment.

4. The aerosol delivery device according to claim 1, wherein the controller activates the aerosol generator if the use of the aerosol delivery device for aerosol treatment is detected by the sensor.

5. The aerosol delivery device according to claim 1, wherein the sensor detects the use of the aerosol delivery device for aerosol treatment by sensing a contact between the aerosol delivery device and a user.

6. The aerosol delivery device according to claim 1, wherein the controller operates the aerosol generator in a pulsed mode after deactivation of the aerosol generator.

7. The aerosol delivery device according to claim 6, wherein aerosol generation pulses have pulse durations in a range of 0.001 s to 10 s.

8. The aerosol delivery device according to claim 6, wherein aerosol generation pulses are provided at time intervals in a range of 0.001 s to 10 s.

9. The aerosol delivery device according to claim 6, wherein aerosol generation pulses have pulse durations in a range of 0.01 s to 5 s.

10. The aerosol delivery device according to claim 6, wherein aerosol generation pulses are provided at time intervals in a range of 0.01 s to 5 s.

11. The aerosol delivery device according to claim 1, further comprising a monitoring unit which monitors an operating ability of the aerosol generator.

12. The aerosol delivery device according to claim 1, wherein the period of time is in a range of 0.1 s to 10 min.

13. The aerosol delivery device according to claim 1, wherein the period of time is in a range of 2 s to 1 min.

14. The aerosol delivery device according to claim 1, wherein the period of time is in a range of 3 s to 30 s.

15. A method for operating an aerosol delivery device, comprising:

operating an aerosol generator for generating an aerosol in the aerosol delivery device, detecting a use of the aerosol delivery device for aerosol treatment using a sensor, and deactivating the aerosol generator by means of a controller if no use of the aerosol delivery device for aerosol treatment is detected by the sensor, wherein the aerosol generator is deactivated after the lapse of a period of time if no use of the aerosol delivery device for aerosol treatment is detected by the sensor, wherein the sensor detects the use of the aerosol delivery device for aerosol treatment by sensing a user's regular respiration, including both inhalation and exhalation, through the aerosol delivery device, and wherein the aerosol generator is a vibrating membrane nebulizer.

16. The method for operating an aerosol delivery device according to claim 15, wherein the period of time is in the range of 1 s to 5 min.

17. The method for operating an aerosol delivery device according to claim 15, further comprising the step of activating the aerosol generator using the controller if the use of the aerosol delivery device for aerosol treatment is detected by the sensor.

18. The method for operating an aerosol delivery device according to claim 15, wherein the use of the aerosol delivery device for aerosol treatment is detected by sensing a contact between the aerosol delivery device and a user.

19. The method for operating an aerosol delivery device according to claim 15, further comprising the step of operating the aerosol generator in a pulsed mode after deactivation of the aerosol generator.

20. The method for operating an aerosol delivery device according to claim 19, wherein aerosol generation pulses have pulse durations in a range of 0.001 s to 10.

21. The method for operating an aerosol delivery device according to claim 19, wherein aerosol generation pulses are provided at time intervals in a range of 0.001 s to 10.

22. The method for operating an aerosol delivery device according to claim 19, wherein aerosol generation pulses have pulse durations in a range of 0.01 s to 5 s.

23. The method for operating an aerosol delivery device according to claim 19, wherein aerosol generation pulses are provided at time intervals in a range of 0.01 s to 5 s.

24. The method for operating an aerosol delivery device according to claim 15, wherein the period of time is in a range of 0.1 s to 10 min.

25. The method for operating an aerosol delivery device according to claim 15, wherein the period of time is in a range of 2 s to 1 min.

26. The method for operating an aerosol delivery device according to claim 15, wherein the period of time is in a range of 3 s to 30 s.

* * * * *